US005538652A

United States Patent [19]
Farng et al.

[11] Patent Number: 5,538,652
[45] Date of Patent: Jul. 23, 1996

[54] DIMERCAPTOTHIADIAZOLE-MERCAPTAN COUPLED COMPOUNDS AS MULTIFUNCTIONAL ADDITIVES FOR LUBRICANTS AND FUELS

[75] Inventors: Liehpao O. Farng, Lawrenceville; Arjun K. Goyal, Woodbury, both of N.J.

[73] Assignee: Mobil Oil Corporation, Fairfax, Va.

[21] Appl. No.: 328,971

[22] Filed: Oct. 24, 1994

Related U.S. Application Data

[63] Continuation of Ser. No. 55,095, May 3, 1993, abandoned.

[51] Int. Cl.$^6$ .................... C10M 135/36; C10L 1/24; C07D 285/12
[52] U.S. Cl. ................. 508/231; 44/342; 548/142
[58] Field of Search ................ 548/142; 252/47

[56] References Cited

U.S. PATENT DOCUMENTS

| | | | |
|---|---|---|---|
| 2,719,125 | 9/1955 | Roberts | 252/46.7 |
| 2,765,289 | 10/1956 | Fields et al. | 252/32.7 |
| 3,775,321 | 11/1973 | Turnquest et al. | 252/47 |
| 3,909,420 | 9/1975 | Turnquest et al. | 252/47 |
| 3,966,623 | 6/1976 | Krug et al. | 252/47 |
| 4,104,179 | 8/1978 | Colclough | 252/47 |
| 4,871,465 | 10/1989 | Hutchison | 252/47 |
| 5,075,020 | 12/1991 | O'Connor | 252/47 |
| 5,275,630 | 1/1994 | Dorer | 44/341 |

*Primary Examiner*—Ellen M. McAvoy
*Attorney, Agent, or Firm*—Ronald A. Bleeker; Malcolm D. Keen

[57] ABSTRACT

Combinations of dimercaptothiadiazole-mercaptan coupled derivatives with amines have been found to be effective load-carrying additives for lubricants and fuels.

18 Claims, No Drawings

5,538,652

DIMERCAPTOTHIADIAZOLE-MERCAPTAN COUPLED COMPOUNDS AS MULTIFUNCTIONAL ADDITIVES FOR LUBRICANTS AND FUELS

This is a continuation of application Ser. No. 08/055,095, filed on May 3, 1993, now abandoned.

BACKGROUND OF THE INVENTION

1. Field of the Invention

This invention is directed to combinations of dimercaptothiadiazole-mercaptan coupled dithio compounds with amines which have proven to be highly effective multifunctional antiwear/extreme pressure additives for lubricants and fuels.

2. Description of Related Art

Dimercaptothiadiazole derivatives, such as 2,5-dimercapto-1,3,4-thiadiazole, disodium 2,5-dimercaptothiadiazole, and 2,5-bis(t-nonyl-dithio) thiadiazole, are well known for their antioxidancy, anticorrosion, and metal passivation properties in a variety of lubricant applications, as disclosed in U.S. Pat. Nos. 4,661,273, 4,678,592 and 4,584,114.

Furthermore, U.S. Pat. No. 5,186,850 discloses that the incorporation of the heterocyclic dimercaptothiadiazole functionality into succinimide structures provides ashless dispersants with multifunctional antiwear, antioxidant and corrosion inhibitor properties in lubricant compositions. Additionally, various reaction products of mercapto- and dimercaptothiadiazoles have been known to possess extreme pressure/antiwear properties, in a variety of lubricant formulations, as exemplified in U.S. Pat. Nos. 4,661,273; 4,382,869; and 4,678,592.

The use of amines in lubricants and the detergent industry has been well known for their alkalinity, surface activity, and neutralization capability. Amine phosphate is one class of additives used extensively in industrial oils, and polyamine-derived succinimides are key components in ashless dispersants of engine oils.

Reaction products of dimercaptothiadiazole derived alcohols and alkenyl succininic anhydrides and their subsequent amine reaction products have been found to be effective antiwear/antioxidant additives for lubricants; see U.S. Pat. No. 4,908,144. U.S. Pat. No. 5,188,746 discloses antiwear/antioxidant additives for lubricants based on dimercaptothiadiazole derivatives of acrylate and methacrylate polymers and amine reaction products thereof.

It has now been found that the use of these combinations of thiadiazole-derived dithio additives with amine derivatives, in accordance with the present invention, provide exceptional antiwear/EP activity with significantly enhanced metal passivating/corrosion inhibiting properties for lubricants and fuels.

BRIEF SUMMARY OF THE INVENTION

Lubricant and fuel compositions in accordance with the invention containing small additive concentration of a combination of a dimercaptothiadiazole-mercaptan coupled compound with an amine product possess excellent antiwear properties coupled with good extreme pressure activities. Additional antioxidation, cleanliness, antifatigue, high temperature stabilizing, and friction modifying properties are likely. Both the thiadiazole-dithio moiety and the amine/ammonium salt moiety are believed to provide the basis for the synergistic antiwear and EP property of these novel additives.

All of these beneficial properties are believed to be enhanced as a result of this novel internal synergism. This unique internal synergism concept is believed to be applicable to similar structures containing (a) thiadiazole groups, (b) dithio linking groups, (c) amine groups within the same component. The products of this invention show good stability and compatibility when used in the presence of other commonly used additives in fuel or lubricant compositions.

These remarkable benefits are also expected for a variety of synthetic and mineral oil based lubricants and fuels particularly light distillate fuels containing these additives. The compositions of matter and the lubricant and fuel compositions are believed to be novel. To the best of our knowledge, these compositions have not been previously used as antiwear/extreme pressure additives in lubricating oils, greases, or fuel applications.

More specifically this invention is directed to improved lubricant or fuel compositions comprising a major proportion of an oil of lubricating viscosity or a grease prepared therefrom, or a major proportion of a liquid hydrocarbyl or hydrocarboxy fuel and a minor proportion of a multifunctional antiwear/extreme pressure additive product of reaction consisting of combinations of dimercaptothiadiazole-mercaptan coupled dithio compounds with hydrocarbyl amines.

DESCRIPTION OF THE PREFERRED EMBODIMENTS

Preparation 2,5-dimercapto-1,3,4-thiadiazole (DMTD), made by the reaction of hydrazine with carbon disulfide) oxidatively coupled with alkyl mercaptans, such as nonyl, to form thiadiazole-derived dithio compounds (Structure A). These dithio adducts were then blended with various amines to form a new group of additive blends.

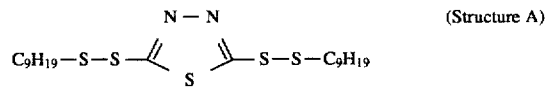

(Structure A)

However, applicants do not wish to be bound by a particular structure(s) or formula for the additive reaction products in accordance with the invention [Structure (s) B] i.e., the combination of the dithio adducts blended with the various amines.

The mercaptothiadiazoles may be prepared as above or made in any convenient manner or obtained as an article of commerce. Any suitable mercaptothiadiazole such as 2,5-dimercapto-1,3,4-thiadiazole; 3,5-dimercapto-1,2,4-thiadiazole; 4,5-dimercapto-1,2,5- thiadiazole; etc. Accordingly, the hydrocarbyl groups need not be alkyl or limited to $C_9H_{19}$ but may be R as in the below generalized structure:

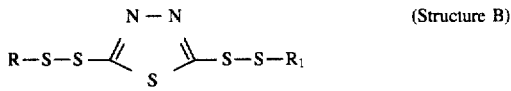

(Structure B)

where R and $R_1$ can be the same or different and are hydrogen or $C_1$ to about $C_{30}$ hydrocarbyl selected from alkyl, aryl, aralkyl, alkaryl and may optionally contain additional O, S, or N or mixtures thereof. Preferably R is $CnH_{2n+1}$, where n is 1 to about 30.

Mercaptobenzothiazoles such as 6,7-dimercaptobenzo-2,1,3-thiadiazole are also believed to be suitable.

Generally, the amines used in this invention are aliphatic and can be primary, secondary, or tertiary and preferably alkylamines or arylamines.

Non-limiting examples of primary amines are methylamine; ethylamine; n-propylamine; isopropylamine; n-butylamine; dodecylamine; triacontylamine; allylamine; 2-propynlamine; cyclohexylamine; propargylamine; isobutylamine; sec-butylamine; 2-ethylhexylamine; cyclopropylmethylamine; t-butylamine; 1,1-dimethyl-2-propynlamine; 1,1-diethyl-2-propynylamine; 1-ethynylcyclohexylamine and benzylamine.

Non-limiting examples of secondary amines are dimethylamine, diethylamine, dibutylamine, diotylamine, ditetradecylamine, diallylamine, di-2-hexenylamine, dicyclohexylamine, methylethylamine, methyl cyclohexylamine, diisopropylamine, diisopentylamine, ethyl cyclohexylamine, (3-amine-propyl)alkenylamine wherein the alkenyl group has 16 to 18 carbon atoms; (3-aminopropyl) alkenylamine wherein the alkenyl group has 18, 20 and 22 carbon atoms; and dihydrogenated tallow amine (e.g. Armeen 2HT).

Non-limiting examples of tertiary amines are trimethyamine, dimethyl ethylamine, triethylamine, tributylamine, trioctylamine, triallylamine, triisopentylamine, tricyclohexylamine, dimenthyl octylamine, n-hexadecyldimethylamine, (e.g. Armeen DM16D) n-octadecyl-dimethylamine (e.g. Armeen DM18D), methyl dihydrogenated tallowamine (e.g. Armeen M2HT), and methyl dicocoamine (e.g. Armeen M2C).

Non-limiting examples of arylamines are aniline 2-chloroaniline; 3-chloroaniline; 4-chloroaniline; 2-methyl-4-chloroaniline; 2,4-dichloroaniline; 3,4-dichloroaniline; 2,5-dichloro-4-nitroaniline; m-tri-fluoromethylaniline; isopropulaniline; p-methoxyaniline; N-methoxymethyl-2,6-diethylaniline; a-naphthylamine; N-sec-butl-4-t-butyl-2,6-dinitroaniline; 3-amino-2,5-dichlorobenzoic acid; N,N-dipropyl, a,a,a-trifluoro-2,6-dinitro-p-toluidine; 4-bromo-3-chloroaniline; 4(4'-chlorophenoxy) aniline; $N^3$, $N^3$-diethyl-2,4-dinitro-6-trifluoromethyl-m-phenylenediamine; p-dimethylaminoaniline; diphenylamine; p-bromoaniline; m-aminophenyl-t-butylcarbamate; o-phenylenediamine; m-phenylenediamine; 4-dimethylamino-3,5-dimethylphenol; 4-(methylsulfonyl)-2,6-dinitro-N,N-dipropylaniline; 3,5-dinitro-N,N-dipropylsulfanilamide; N-sec-butyl-4-t-butyl-2,6-dinitroaniline; m-toluisine; p-toluidine; m-t-butylaniline; o-anisidine; p-anisidine; dimethylaniline; o-nitroaniline; p-nitroaniline; and 4,4'-oxydianiline.

Non-limiting examples of heterocyclic amines are 3-amino-1,2,4-triazole; 2-chloro-4-ehtylamino-6-isopropylamino-s-triazine; pyridine; piperidine; piperazine; morphiline; 4,4'-dipyridyl; 8-hydroxyquinoline; 4-amino-6-t-butyl-3-(methykthio)-1,2,4-triazine-5(4H)-one; 6-ethoxy-1,2-dihydro-2,2,,4-trimethylquinoline; indole; hexahydro-1H-azepine; 4-amino-5-chloro-2-pheyl-3(2H)-pyridazinone; pyrrole; imidazolidine; isoquinoline; 2,4-lutidine; 2-methyl-5-ethylpyridine; 2-dimethyl aminopyridine; a-picoline; B-picoline; y-picoline; quinoline; and 4,4'-dipyridine.

Non-limiting examples of other salt forming amino compounds contemplated are 2-chloroethyl dimethylamine; diethanilaminel guanidine; dodecylguanidine; 3-(4-chlorophenyl)-1,1-dimethylurea, 3-(3,4,-dichlorophenyl)-1,1-dimethylurea, Fenuron; Tandex; B-alanine; methyl glycine; glycinamide; aminoacetonitrile; aminoethanthiol; aminoacetic acid; diethyl ethanolamine; diethylenetriamine; isopropanolamine; diisopropanolaminel triisopropanolamine; ethylenediamine; hexamethylenetetramine; hydrazine; phenothiazine; sulfanilic acid; tetraethylenepentamine; thiourea; urea; triethanolamine; triethylenetetramine; diethanol soyaamine (e.g. Ethomeen S-12) and didecaoxyethylene soyaamine (e.g. Ethomeen S-20).

Examples of highly suitable amines are:

a) cyclic amines: dicyclohexylamine, 1,4-diaminocyclohexane, piperidine, hexamethyleneimine, etc.;

b) heterocyclic amines: morpholine, aminopropyl morpholine (APM), aminoethyl piperazine (AEP);

c) etheramines: $C_6$ to $C_{13}$ alkyloxypropylamines (Exxon and Sherex), polyoxyalkylene amines (Texaco Jeffamine);

d) diamines: Exxon etherdiamines (DA-14, DA-17), Texaco polyoxyalkylene diamine, Akzo Duomeens (Duomeen C&O);

e) straight chain amines: ethylamine, propylamine, butylamine, pentylamine, hexylamine, dioctylamine, dicocoamine, etc.;

f) branched chain amines: 2-ethylhexylamine, isopropylamine, isobutylamine, diisobutylamine, bis(2-ethylhexyl)amine, tert-alkyl amine(C18–C22), dicocoalkyl-methylamine.

An excess of one reagent or another can be used. Molar quantities, less than molar quantities, or more than molar quantities of either amines or dithio-adducts can be used.

Conditions for the above reactions may vary widely depending upon specific reactants, the presence or absence of a solvent and the like. Any suitable set of reaction conditions known to the art may be used. Hydrocarbon solvents such as toluene or xylenes are frequently used. Generally stoichiometric or equimolar ratios of reactants are used. However, more than molar or less than molar amounts may be used. In any event, reaction conditions are not viewed as critical. Generally speaking, the reaction temperature may vary from ambient to about 250° C. or reflux, the pressure may be autogenous or vary from ambient to about 100 psi with reaction times varying from about one hour to about 48 hours or more.

Clearly the use of additive concentrations of these dithio adducts coupled with various amines provide exceptional antiwear, load-carrying activity and corrosion inhibiting properties, etc. when incorporated into fuel and lubricant compositions.

The additives embodied herein are utilized in lubricating oil or grease compositions in an amount which imparts significant antioxidant, load-carrying and corrosions inhibiting characteristics to oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %. It is expected that these materials would also be suitable for use in liquid hydrocarbyl or alcoholic or mixed hydrocarbyl/alcoholic fuel compositions. They are generally utilized in amounts varying from about 50 to about 500 pounds per 1000 barrels of fuel.

The additives have the ability to improve the antiwear characteristics and friction reducing characteristics of various oleagenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

It is to be understood, however, that the compositions contemplated herein can also contain other materials. For example, corrosion inhibitors, extreme pressure agents and the like can be used as exemplified respectively by metallic phenates sulfonates, polymeric succinimides, non-metallic or metallic phosphorodithioates and the like. These materials do not detract from the value of the compositions of this invention, rather the materials serve to impart their customary properties to the particular compositions in which they are incorporated.

The following examples are merely illustrative and are not meant to be limitations on the scope of this invention.

EXAMPLE 1

Approximately 95 gm of 2,5-bis(t-nonyl-dithio)thiadiazole (commercially obtained from Amoco Chemical Company under the tradename Amoco 158 or from Mobil Chemical Company under the tradename Mobilad C-610) and 5 gm of isodecyloxypropylamine (commercially obtained from Sherex Chemical Company under the tradename Adogen 180) were blended together in a mixer at 80° C. for two hours. After a quick filtration, approximately 99.5 gm of yellow-brown liquid was recovered as desired blending product.

EXAMPLE 2

Approximately 90 gm of 2,5-bis(t-nonyl-dithio)thiadiazole and 10 gm of isodecyloxypropylamine were blended together in a mixer at 80° C. for two hours. After a quick filtration, approximately 99.2 gm of yellow-brown liquid was recovered as desired blending product.

EXAMPLE 3

The reaction procedure of Example 2 was followed with one exception: $C_{18-22}$ tert-alkyl primary amine (commercially obtained from Rohm Haas Chemical Company under the tradename Primene JM-T) was used instead of isodecyloxypropylamine.

EXAMPLE 4

The reaction procedure of Example 1 was followed with one exception: oleyl 1,3-diaminopropane (commercially obtained from AKZO Chemical Company under the tradename Duomeen O) was used instead of isodecyloxypropylamine.

Evaluation

The products of Examples 2, 3 and 4 were blended into industrial oils and evaluated for antiwear performance using the Four-Ball test (Table 1).

TABLE 1

| | Four-Ball Wear Test | |
|---|---|---|
| | Wear Scar Diameter in Mm, 30 Minute Test - 200° F. | |
| Item | 60 Kg 1500 rpm | 40 Kg 1800 rpm |
| Base oil (80% solvent paraffinic bright, 20% solvent paraffinic neutral mineral oils) | 2.12 | 0.733 |
| 1% Mobilad C-610 | 0.784 | 0.600 |
| 1% Example 2 | 0.739 | 0.589 |
| 1% Example 3 | 0.772 | 0.636 |
| 1% Example 4 | 0.794 | 0.609 |

As can be seen from the above wear test results, the product exhibits considerable antiwear activity.

The products of the examples were also blended into fully formulated engine oils: Example 1 was evaluated for load carrying capacity using the Four Ball EP Test (Table 2); Examples 1 and 2 were evaluated in the FZG Gear tester (Table 3).

TABLE 2

Four-Ball EP Test and ASTM Copper Strip corrosion (EP: 1760 rpm/10 sec./25° C.; D130-6:250F/3 h., D130-8:210F/3 h/1% $H_2O$

| Item | Base oil* | Plus 1% Mobilad C-610 | Plus 1% Example 1 |
|---|---|---|---|
| Last Non-seizure Load (kg) | 100 | 100 | 126 |
| Weld Load (Kg) | 200 | 250 | 250 |
| Load Wear Index (LWI) | 41.4 | 46.4 | 53.8 |
| Copper Strip (D130-6) | 2B | 2D | 1A |
| Copper Strip (D130-8) | 2A | 2A | 1A |

*Base oil is a fully formulated synthetic engine oil containing a performance additive package including detergent, dispersant, antioxidant, corrosion inhibitor, and a small amount of zinc dithiophosphate.

TABLE 3

| Item | FZG (pass stage) |
| --- | --- |
| Base oil (fully formulated synthetic oil with additive package containing antioxidant, rust inhibitor, detergent, and dispersant) | 7 |
| Base oil plus 1% Example 1 | 10 |
| Base oil plus 1% Example 2 | 12 |

In the Four Ball Wear Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 52100 steel for thirty minutes under 60/40 kg load at 1500 and 1800 rpm and 200° F. If additional information concerning this test is desired consult test method ASTM D2266 and/or U.S. Pat. No. 4,761,482.

The Copper Strip Corrosivity Test (ASTM D-130) measures a product's propensity to corrode copper due to, for example, contained sulfur groups. Further details may be found in ASTM Standards on Petroleum Products and Lubricants, published annually by the American Society for testing Materials.

The Four-Ball EP Test (ASTM) D-2783) measures the extreme pressure characteristics or load-carrying properties of a lubricant by determining Load Wear Index (LWI) and weld point. A test ball is rotated under load at a tetrahedral position on top of three stationary balls immersed in lubricant. Measurements of scars on the three stationary balls are used to calculate LWI's, and the weld is the load at which the four balls weld together in 10 seconds. The last non-seizure load is the last load at which the measured scar diameter is not more than 5% above the compensation line at the load. The compensation line is a logarithmic plot where the coordinates are scar diameter in millimeters and applied load in kilograms obtained under dynamic conditions. The higher the LWI value the better. See U.S. Pat. No. 4,965,002, which is incorporated herein by reference, and ASTM D-2783.

The FZG Gear Test (DIN-51.354). In this test, dip-lubricated gears are weighed and operated at a fixed speed and fixed initial oil temperature (90° C.) in the gear oil under test. The load on the teeth is increased in increments. After each load stage, the weight changes are determined and recorded. The results are reported in Table 3. The higher the Fail Stage value the better the material. The lower the wear value the better the weight change and/or visual condition. Further details can be found in CEC method L-07-A-71.

As shown above, the products of this invention show very good antiwear, extreme pressure activities as evidenced by improving wear characteristics and scoring load capacity from stage 7 to stage 10–12 in FZG tester, and LWI in Four Ball EP test. In addition, the product of this invention also shows excellent corrosivity control.

The use of additive blends of bis(alkyl-dithio)thiadiazoles and amines in premium quality industrial and engine lubricants will significantly enhance the stability, improve load-carrying, reduce the wear, and extend the service life. These additive blends may also have the potential to benefit gasoline and diesel fuels by improving the antioxidation, antiwear, and anticorrosion characteristics of these fuels. These novel compositions described in this patent information are useful at low concentrations and do not contain any potentially undesirable metals or phosphorus. These dual functional antiwear/EP-antioxidants can be readily commercially made.

What is claimed is:

1. An improved lubricant composition comprising a major proportion of an oil of lubricating viscosity or a grease prepared therefrom, or a liquid hydrocarbyl or hydrocarboxy fuel and a minor proportion of a non-phosphorus, multifunctional antioxidant, load-carrying antiwear/extreme pressure and corrosion inhibiting additive product of reaction comprising a dimercaptothiadiazole coupled dithio compound reacted with a hydrocarbyl amine where each dithio functionality of said dimercaptothiadiazole has attached thereto no more than one hydrogen and at least one $C_1$–$C_{30}$ hydrocarbyl group that are the same or different which results in the additive product having both a thiadiazole-alkyldithio moiety and an amine or ammonium salt moiety and wherein the reaction is carried out at temperatures varying from ambient to about 250° C. under pressures varying from ambient to about 100 psi or is autogenous with the reaction time varying from about one hour to about 48 hours sufficient to obtain the desired additive product of reaction and where the reaction is carried out in molar ratios of reactants varying from equimolar to more than molar to less than molar.

2. The composition of claim 1 wherein said additive product of reaction is generally prepared by reacting a thiadiazole-derived dithio compound of the structural formula

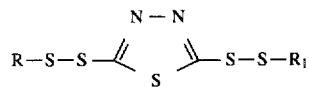

where R and $R_1$ are the same or different and are hydrogen or $C_1$ to about $C_{30}$ hydrocarbyl selected from alkyl, aryl, alkaryl, aralkyl and may optionally contain additional O, S, N or mixtures thereof with a hydrocarbyl amine and wherein the reaction is carried out at temperatures varying from ambient to about 250° C. under pressures varying from ambient to about 100 psi or is autogenous with reaction times varying from about one hour to about 48 hours time sufficient to obtain the desired additive product of reaction and where the reaction is carried out in molar ratios of reactants varying from equimolar to more than molar to less than molar.

3. The composition of claim 1 wherein said dithio compound is 2,5-bis(t-nonyl-dithio)thiadiazole and said amine is isodecyloxypropylamine.

4. The composition of claim 1 wherein said oil of lubricating viscosity is selected from the group consisting of (1) mineral oils, (2) synthetic oils, (3) or mixtures of mineral and synthetic oils or is (4) a grease prepared from any one of (1), (2) or (3).

5. The composition of claim 4 wherein the lubricant contains from about 0.001 to about 10 wt % based on the total weight of the composition of the additive product of reaction.

6. The composition of claim 4 wherein the lubricant is a mineral oil.

7. The composition of claim 4 wherein the lubricant is a synthetic oil.

8. The composition of claim 1 wherein the fuel is selected from the group consisting of liquid hydrocarbyl or hydrocarboxy or alcoholic or mixtures of hydrocarbyl and alcoholic fuels.

9. The composition of claim 8 wherein the fuel contains from about 50 to about 500 lbs. of said additive per 1000 bbs of fuel.

10. The composition of claim 8 wherein the fuel is a distillate fuel.

11. A method of preparing an improved lubricant or fuel composition comprising adding to said lubricant or fuel a minor multifunctional antioxidant, load-carrying, corrosion-inhibiting amount of from about 0.001 to about 10 wt % based on the total weight of the composition or from 50 to about 500 lbs of the additive product of reaction as claimed in claim 1.

12. A method of protecting moving metal parts comprising:
   a) contacting said metal parts with a minor multifunctional antioxidant amount of from about 0.001 to about 10 wt % based on the total weight of the composition or from 50 to about 500 lbs of the additive product of reaction as claimed in claim 1; and
   b) imparting improved load-carrying and corrosion-inhibiting qualities to the moving metal parts contacted with said additive product of reaction of step a).

13. A process of preparing a non-phosphorus multifunctional antioxidant, load-carrying and corrosion inhibiting additive product prepared therefrom, or a liquid hydrocarbyl and a minor proportion of a non-phosphorus, multifunctional antioxidant, load-carrying, antiwear/extreme pressure and corrosion inhibiting additive product of reaction comprising a dimercaptothiadiazole coupled dithio compound reacted with a hydrocarbyl amine where each dithio functionality of said dimercaptothiadiazole has attached thereto no more than one hydrogen and at least one $C_1$–$C_{30}$ hydrocarbyl group that are the same or different which results in the additive product having both a thiadiazole-alkyldithio moiety and an amine or ammonium salt moiety and wherein the reaction is carried out at temperatures varying from ambient to about 250° C. under pressures varying from ambient to about 100 psi or is autogenous with the reaction time varying from about one hour to about 48 hours sufficient to obtain the desired additive product of reaction and where the reaction is carried out in molar ratios of reactants varying from equimolar to more than molar to less than molar.

14. The process of claim 13 wherein wherein said additive product of reaction is generally prepared by reacting a thiadiazole-derived dithio compound of the structural formula

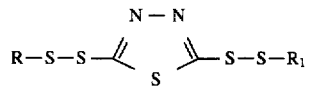

where R and $R_1$ are the same or different and are hydrogen or $C_1$ to about $C_{30}$ hydrocarbyl selected from alkyl, aryl, alkaryl, aralkyl and may optionally contain additional O, S, N or mixtures thereof with a hydrocarbyl amine and wherein the reaction is carried out at temperatures varying from ambient to about 250° C. under pressures varying from ambient to about 10 psi or is autogenous and the reaction time varying from about one hour to about 48 hours sufficient to obtain the desired additive product of reaction and where the reaction is carried out in molar ratios of reactants varying from equimolar to more than molar to less than molar.

15. The process of claim 13 wherein said dithio compound is 2,5-bis(t-nonyl-dithio)thiadiazole and said amine is isodecyloxypropylamine.

16. A lubricant or fuel additive product of reaction consisting of a dimercaptothiadiazole coupled dithio compound reacted with a hydrocarbyl amine where each dithio functionality has attached thereto no more than one hydrogen and at least one $C_1$–$C_{30}$ hydrocarbyl group that are the same or different which results in the additive product having both a thiadiazole-alkyldithio moiety and an amine or ammonium salt moiety and wherein the additive product imparts non-phosphorous multifunctional, load-carrying and corrosion inhibiting qualities to an oil of lubricating viscosity or a grease prepared therefrom.

17. The additive of claim 16 prepared by reacting a thiadiazole-derived dithio compound of the structural formula

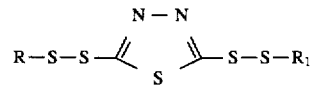

where R and $R_1$ are the same or different and are hydrogen or $C_1$ to about $C_{30}$ hydrocarbyl selected from alkyl, aryl, alkaryl, aralkyl and may optionally contain additional O, S, N or mixtures thereof with a hydrocarbyl amine and wherein the reaction is carried out at temperatures varying from ambient to about 250° C. under pressures varying from ambient to about 10 psi or is autogenous and the reaction time varying from about one hour to about 48 hours sufficient to obtain the desired additive product of reaction and where the reaction is carried out in molar ratios of reactants varying from equimolar to more than molar to less than molar.

18. The additive of claim 16 wherein the reactants are 2,5-bis(t-nonyl-dithio)thiadiazole and isodecyloxypropylamine.

* * * * *